United States Patent [19]
Webber et al.

[11] Patent Number: 5,955,509
[45] Date of Patent: Sep. 21, 1999

[54] PH DEPENDENT POLYMER MICELLES

[75] Inventors: Stephen E. Webber, Austin; Thomas J. Martin, Cedar Park, both of Tex.

[73] Assignee: Board of Regents, The University of Texas System, Austin, Tex.

[21] Appl. No.: 08/842,207

[22] Filed: Apr. 23, 1997

Related U.S. Application Data

[60] Provisional application No. 60/016,790, May 1, 1996.

[51] Int. Cl.$^6$ ............................ A61K 47/34; C08G 68/00
[52] U.S. Cl. ........................ 514/772.7; 528/392; 528/423
[58] Field of Search .................................. 528/392, 423, 528/329; 514/772.5

[56] References Cited

U.S. PATENT DOCUMENTS

| | | | |
|---|---|---|---|
| 4,038,468 | 7/1977 | Sirotkina et al. | 528/392 |
| 5,124,151 | 6/1992 | Viegas et al. | 424/422 |
| 5,143,731 | 9/1992 | Viegas et al. | 424/486 |
| 5,219,564 | 6/1993 | Zalipsky et al. | 424/78.17 |
| 5,399,363 | 3/1995 | Liversidge et al. | 424/490 |
| 5,494,683 | 2/1996 | Liversidge et al. | 424/490 |

FOREIGN PATENT DOCUMENTS 0542133   5/1992   European Pat. Off. .......... 428/402.24

OTHER PUBLICATIONS

Arca, et al., "Release of Hydrophobic Substances from Polystyrene–Methacrylic Acid Block Copolymer Micelles Into Aqueous Media," *Int. J. Polymer Analysis & Characterization*, 2:31–41, 1995.

Kamachi, et al., "Synthesis of Block Polymers for Desalination Membranes, Preparation of Block Copolymers of 2–Vinylpyridine and Methacrylic Acid or Acrylic Acid," *Macromolecules*, 5:161–167, Mar.–Apr. 1972.

Kwon, G.S. & K. Kataoka, "Block Copolymer Micelles as Long–Circulating Drug Vehicles," *Advanced Drug Delivery Reviews*, 16:295–309, 1995.

Kwon, et al., "Micelles Based on AB Block Copolymers of Poly(ethylene Oxide) and Poly(β–Benzyl L–Aspartate)," *Langmuir*, 9 (4) :945–949. 1993.

Nakahama, et al., "Anionic Living Polymerization of Styrenes Containing Electron–Withdrawing Groups," *Makromol. Chem., Macromol. Symp.*, 67:223–236, 1993.

Papahadjopoulos, D. & A. Gabizon, "Lipsomes Designed to Avoid the Reticuloendothelial System," in *Horizons in Membrane Biotechnology*, (C. Niclau and D. Chapman, Eds.; wiley–Liss, Inc.: NY, pp. 85–93, 1990.

Ropert, et al., "Olignucleotides Encapsulated in pH Sensitive Liposomes Are Efficient Toward Friend Retrovirus," *Biochemical & Biophysical Research Comm.*, 183 (2):879–885, Mar. 1992.

Seki, K. & D.A. Tirrell, "pH–Dependent Complexation of Poly(Acrylic Acid) Derivatives With Phospholipid Vesicle Membranes," *Macromolecules*, 17:1692–1698, 1984.

Thomas, J.L. & D.A. Tirrell, "Polyelectrolyte–Sensitized Phosphlipid Vesicles," *Acc. Chem. Res.*, 25:336–342, 1992.

*Primary Examiner*—Peter F. Kulkosky
*Attorney, Agent, or Firm*—Denise L. Mayfield; Locke Liddell & Sapp LLP

[57] ABSTRACT

The present invention relates to the use of poly(vinyl N-heterocycle)-block-poly(alkylene oxide) copolymers in micelle containing pharmaceutical formulations. The copolymers advantageously respond to pH differences in the environment to which they are exposed forming micelles at higher pH values. The micelles, which comprise a therapeutic compound and a copolymer, deliver drug in a pH dependent manner.

10 Claims, 3 Drawing Sheets

PH DEPENDENT POLYMER MICELLES

The present application claims priority to Provisional Application U.S. Ser. No. 60/016,790, filed May 1, 1996.

BACKGROUND OF THE INVENTION

1. Field of the Invention

The present invention relates to pH dependent polymer micelles used for the encapsulation of hydrophobic organic compounds. The invention relates more specifically to the encapsulation of hydrophobic drugs in micelles for use in drug delivery.

2. Description of the Related Art

Micelles have been prepared by a wide variety of methods using an equally diverse group of compounds. Polymers have been used to form micelles for drug delivery. Such micelle forming polymeric drug formulations have generally been designed to behave in a pH independent manner and have comprised nonionic polymers or copolymers. E. Arca et al., *Int. J. Polymer Analysis & Characterization* (1995), 2, pp. 31–41; C. Ropert et al., *Biochem. Biophys. Res. Commun.* (1992), 187(2), pp. 379–885; K. Seki et al., *Macromolecules* (1984), 17, pp. 1692–1698; D. Collins and L. Huang in *Molecular Mechanisms of Membrane Fusion* (S. Ohki, D. Doyle, T. Flanagan, S. Hui and E. Mayhew, Eds; Plenum Press: N.Y. (1988), pp 149–161); D. Papahadjopoulos and A. Gabizon in *Horizons in Membrane Biotechnology* (C. Nicolau and D. Chapman, Eds; Wiley-Liss: N.Y. (1990), pp. 85–93); and G. S. Kwon and K. Kazunori, *Adv. Drug Delivery Reviews* (1995), 16, 295–309. The prior art polymers have generally been block copolymers.

The primary drawbacks of those methods has been lack of sufficient drug loading as well as lack of tissue targeting which is particularly important in the chemotherapeutic treatment of neoplasia related diseases such as cancer and tumors. Additionally, prior art formulations have not been based on pH sensitive poly(vinyl N-heterocycle) containing copolymers.

Even though various methods have been developed to deliver hydrophobic drugs, no single method has been found to be universally applicable and have a high success rate. Delivery of hydrophobic drugs resulting in increased bioavailability and/or preferred tissue targeting remains a problem to the pharmaceutical industry.

Accordingly, there is a need to develop more efficacious drug delivery methods for the delivery of hydrophobic drugs. Specifically, there is a need for formulations capable of forming stable micelles under a first physiological condition, such as high pH, and having the micelles disrupted under a second physiological conditions, such as low pH.

It is an object of the present invention to provide a formulation comprising the diblock copolymer poly(vinyl N-heterocycle)-block-poly(alkylene oxide) and a pharmacologically active compound, where the copolymer is capable of forming micelles in a pH dependent manner in an aqueous medium.

It is another object of the present invention to provide a formulation comprising a pharmacologically active compound and a poly(vinyl N-heterocycle)-block-poly(alkylene oxide) copolymer which will form micelles in a water containing medium when the copolymer is in an environment having a pH where the N-heterocycle nitrogen(s) is unprotonated.

It is yet another object of the present invention to provide a formulation comprising a pharmacologically active compound and a poly(vinyl N-heterocycle)-block-poly(alkylene oxide) copolymer which will form micelles when the N-heterocycle containing block is unprotonated and not form micelles when the N-heterocycle containing block is protonated. It is still yet another object of the present invention to provide a formulation comprising micelles which comprise a pharmacologically active compound and a poly(vinyl N-heterocycle)-block-poly(alkylene oxide) copolymer having pH dependent properties. Another object of the present invention to provide a micelle containing formulation wherein the micelle comprises a pharmacologically active compound and a poly(vinyl N-heterocycle)-block-poly(alkylene oxide) copolymer that forms micelles at higher than physiological pH values and does not form micelles at lower than physiological pH values.

It is a still further object of the present invention to provide a micelle containing pharmaceutical formulation, the micelle comprising a relatively hydrophobic therapeutic compound and a poly(vinyl pyridine)-block-poly(ethylene oxide) copolymer having pH dependent properties. A further object of the present invention to provide a micelle containing pharmaceutical formulation having pH dependent properties, the micelle comprising a relatively hydrophobic therapeutic compound, a poly(vinyl N-heterocycle) homopolymer and a poly(vinyl N-heterocycle)-block-poly(alkylene oxide) copolymer.

SUMMARY OF THE INVENTION

The present invention is directed to micelle containing formulations that comprise a pharmacologically active compound and a poly(vinyl N-heterocycle)-block-poly(alkylene oxide) copolymer having pH dependent properties. The unique pH dependent formation of micelles characteristic of the present formulations make them particularly useful for controlled delivery of pharmacologically active agents, particularly therapeutic agents.

Without intending to be limited to any particular mechanism of action, the invention accomplishes the controlled release of pharmacologically active agents by providing a formulation containing micelles that include a pharmacologically active agent which is released from the micelle as a function of pH. Generally speaking, the micelles of the various formulations remain intact at higher pH values. Release of the pharmacologically active agent may be selectively prevented simply by manipulating the pH of the environment into which the formulation is introduced. Upon a relative decrease in pH (relative to the pH of the surrounding environment, for example tissue or fluid), the micellular formations in the preparation break down.

The terms "high" pH and "low" pH as used in the description of the present invention are relative terms. For example, a high pH value may be defined as a pH that is a value greater or about equal to the pKa of the nitrogens that comprise the poly(vinyl N-heterocycle) of the polymer of the micelle containing formulation. A low pH value as used in the definition of the invention is a pH that is below or less than the pKa of the nitrogens that comprise the poly(vinyl N-heterocycle) of the polymer of the micelle containing formulation.

The formulations of the invention are intended to include any formulation wherein about 5% to about 10% by volume of the formulation comprises the pH dependent micelles as described herein. However, formulations that include 20%, 30%, 40%, 50%, 60%, 70%, 80%, 90% or even about 95% by volume polymeric micelles are also contemplated by the present invention. Both water soluble and non-water soluble pharmacologically active agents may be employed in the invention. By way of example and not limitation, it is anticipated that the invention will be useful in the delivery of anti-cancer drugs to target tissues, such anti-cancer drugs that are well-known to those of skill in the art. Such anti-cancer agents are described in Goodman and Gilman's, The Pharmacological Basis of Therapeutics (18th ed.) (1990), which reference is specifically incorporated herein by reference.

More specifically, while again not intending to be limited to any mechanism or theory of action, the pH dependent behavior of micelle formation is dictated by the basicity of the N-heterocycle nitrogen(s) of the polymers that make up the micelle. At lower pH values, the N-heterocycle will be protonated, thereby forming a very hydrophilic diblock copolymer. This hydrophilic diblock copolymer is soluble in water containing medium. At higher pH values, the N-heterocycle of the polymeric composition will be unprotonated, thereby forming an amphoteric diblock copolymer. This amphoteric diblock copolymer will aggregate into micelles. The N-heterocyclic portion of the copolymer forms the core of the micelle, while the alkylene oxide portion forms the shell of the micelle. When pH decreases sufficiently to permit the existence of the protonated N-heterocycle, there will be a decrease in micelle content volume in the formulation. As pH increases, the unprotonated N-heterocycle species will exist, resulting in the aggregation of the polymer into the described micelles. The pKa of the polymer and the heterocycle will dictate the micelle formation in the presently described formulations. The pKa of the polymer and the pKa of the heterocycle may and frequently will differ.

It is contemplated that the present invention provides pharmaceutical formulations that are suitable for administration in any of a variety of methods known to the skilled artisan, such as by oral, intravenous or intraperotineal administration. It is also contemplated and within the scope of the present invention that the pharmaceutical formulation may contain more than one therapeutic compound. It is further contemplated and within the scope of the present invention that the pharmaceutical formulation may be used in either a rapid or sustained release dosage form.

The scope of the present invention also provides pharmaceutical formulations that may be used for the targeted delivery of therapeutic compounds to specific biological tissues.

In one embodiment of the invention, the micelle containing formulation comprises a pharmacologically active therapeutic compound, and a poly(vinyl N-heterocycle)-block-poly(alkylene oxide) copolymer, where the ability of the copolymer to form micelles is pH dependent, so that micelles will form at higher pH values but not at lower pH values. By way of example, micelle formation may occur in some embodiments of the formulation at a pH above about 5 to about 10. Below a pH of about 5, some embodiments of the formulations of the invention would have a reduced volume of micelles. This is because at relatively lower pH, the micelles would disassemble, releasing the pharmacologically active agent included therein.

In another embodiment, the present invention provides a micelle-containing pharmaceutical formulation that is capable of maintaining micellular form at a pH characteristic of the blood stream (pH about 6.75). In some of the formulations, the micelles are designed to dissipate in an environment of a lower pH, such as upon contact with or inclusion into an appropriate targeted tissue, such as a cancer, carcinoma or tumor. Cancer tissue is hypoxic. The pH of cancer tissue generally is relatively lower than blood. The pH of cancer cells varies widely, and has been recognized as having a pH as low as about 4.5. The micelle formulations of the invention therefore provide a convenient technique for targeting a pharmaceutically active agent to a cancer or other relatively low pH tissue via a blood carrier.

In another embodiment, the invention comprises a capsule that comprises a micelle-containing formulation within an enteric coating. These formulations are suitable for oral administration and are expected to minimize premature gastric release of the pharmacologically active agent or therapeutic compound.

In some embodiments, the micelle containing formulations comprise a therapeutic compound and a poly(vinyl N-heterocycle)-block-poly(ethylene oxide) copolymer having the pH dependent properties described above.

In other embodiments of the invention, the micelle containing formulations comprise a pharmaceutical preparation that comprises a therapeutic compound, a poly(vinyl N-heterocycle) homopolymer and a poly(vinyl N-heterocycle)-block-poly(ethylene oxide) copolymer having pH dependent properties. In some embodiments, the micelle containing pharmaceutical formulation comprises a hydrophobic drug, a poly(vinylpyridine) homopolymer and a poly(vinyl pyridine)-block-poly(ethylene oxide) copolymer.

In another aspect of the invention, a process for the preparation of a micelle containing pharmaceutical formulation is provided. In some embodiments, the process comprises combining a pharmacologically active agent, particularly a therapeutic compound, with a poly(vinyl N-heterocycle)-block-poly(alkylene oxide) copolymer having pH dependent properties capable of forming micelles at high pH relative to the pKa of the polymer.

In another embodiment, the process comprises contacting a therapeutic compound with a poly(vinyl pyridine) homopolymer and a poly(vinyl N-heterocycle)-block-poly (alkylene oxide) copolymer having pH dependent properties to form micelles.

The copolymers used in the micelle containing pharmaceutical formulation of the present invention include copolymers of the formula I Formula I and all its isomeric, chiral, pharmaceutically acceptable salt, oligomeric, polymeric, diastereomeric and/or racemic forms, wherein:

$R_1$ is H or a polymerization initiator selected from:
cumyl, s-butyl, n-butyl, 1,1-diphenylethyl, 1-phenyl-1-naphthylethyl, 1-phenyl-1-phenanthrylethyl, 1-anthracyl-phenylethyl, 2-phenylpropyl or diphenylmethyl;

$R_2$ is selected from the group consisting of:

-continued where, for the structures containing an $R_4$ substituted nitrogen, $R_4$ may be absent from the nitrogen and $R_2$ may attach to the structure backbone by way of the nitrogen;

$R_3$ is H or C1–C5 alkyl;

$R_4$ is C1–C5 alkyl when $R_2$ is attached to the copolymer backbone by an atom other than the nitrogen to which $R_4$ is attached;

$R_5$ is H or C1–C5 alkyl attached to any carbon on $R_2$;

m is independently selected at each occurrence from 50 to 500; and n is independently selected at each occurrence from 50 to 500;

to provide a chemically stable compound.

The homopolymers used in micelle containing pharmaceutical formulation of the present invention include copolymers of the formula II $$R_1\text{—}[CH_2CH(R_2)]_m\text{—}H \qquad \text{Formula II}$$

and all its isomeric, chiral, pharmaceutically acceptable salt, oligomeric, polymeric, diastereomeric and/or racemic forms wherein:

$R_1$ is H or a polymerization initiator selected from:
cumyl, s-butyl, n-butyl, 1,1-diphenylethyl, 1-phenyl-1-naphthylethyl, 1-phenyl-1-phenanthrylethyl, 1-anthracyl-1-phenylethyl or diphenylmethyl;

$R_2$ is selected from the group consisting of:

where, for the structures containing an $R_4$ substituted nitrogen, $R_4$ may be absent from the nitrogen and $R_2$ may attach to the structure backbone by way of the nitrogen;

$R_4$ is C1–C5 alkyl when $R_2$ is attached to the copolymer backbone by an atom other than the nitrogen to which $R_4$ is attached;

$R_5$ is H or C1–C5 alkyl attached to any carbon on $R_2$; and m is independently selected at each occurrence from 50 to 500;

to provide a chemically stable compound.

It is understood that the substituents included in $R_2$ possess different basicities. Therefore, it is contemplated and within the scope of the invention that the compounds of formula I and formula II may be utilized in a broad range of pH values and still exhibit the necessary pH dependent micelle forming behavior.

It should be understood that the particular combinations of $R_2$ and $R_3$ will result in various compounds of the formula I, each possessing its particular combination of properties. As a result, one particular combination of $R_2$ and $R_3$ may be best suited for a first therapeutic compound while another combination of $R_2$ and $R_3$ may be best suited for a second therapeutic compound. Methods for the selection of a particular therapeutic compound/formula I compound combination follow below. Methods for the selection of a particular therapeutic compound/formula I compound/formula II compound combination follow below.

Other features, advantages and embodiments of the invention will be apparent to those skilled in the art from the following description, accompanying data and appended claims.

DETAILED DESCRIPTION OF THE INVENTION

The use of the pH dependent poly(vinyl N-heterocycle)-block-poly(alkylene oxide) copolymers of formula I for the preparation of micelle containing pharmaceutical formulations has distinct advantages over the prior art. The present formulations exhibit a pH dependent micelle formation unlike that of prior art polymers or copolymers. When in the blood stream, the present formulations should retain their micellular structure until they are exposed to a lower pH environment; thus they can be used to target delivery of drugs to tissues having a pH lower than that of the blood. Provided they are formulated so as to avoid gastric exposure, the present formulations should retain their micellular structure throughout the intestinal tract even as they cross the intestinal wall and enter the blood stream.

As used herein, the term "poly(alkylene oxide)" includes all oligomers and polymers which are comprised of repeating units of allylene oxide. The present invention includes all the isomeric, diastereomeric, chiral, racemic, oligomeric and polymeric forms of the poly(alkylene oxides) included in the compounds of formula I above. The poly(allylene oxides) used in the invention may possess a wide range of molecular weights.

The poly(alkylene oxides) comprising the pH dependent diblock copolymers of the present formulation are available commercially or may be made by a variety of methods, such as described below or disclosed in *Poly(ethylene glycol) Chemistry: Biotechnical and Biomedical Applications* (J. M. Harris, Ed.; Plenum Press, N.Y.) the teachings of which are hereby incorporated by reference.

The term "alkylene oxide" refers to alkyl compounds containing two to seven carbons and having an epoxide or oxirane ring at one end. The alkylene oxides which may be used in the invention include, by way of example and without limitation, ethylene oxide, propylene oxide, butylene oxide, 1,2-epoxypentane, 1,2-epoxyhexane and 1,2-epoxyheptane.

As used herein, the term "poly(vinyl N-heterocycle)" includes all oligomers and polymers comprised of repeating units of vinyl N-heterocycles. The present invention includes all the isomeric, diastereomeric, chiral, racemic, oligomeric and polymeric and pharmaceutically acceptable salt forms of the poly(vinyl N-heterocycles) included in the compounds of formula I and formula II above. The poly (vinyl N-heterocycles) useful in the invention may possess a wide range of molecular weights. The molecular weight of the poly(vinyl N-heterocycle) will affect the aggregation number of the micelles such that increasing molecular weight will increase the aggregation number.

The poly(vinyl N-heterocycles) comprising the pH dependent diblock copolymers of the present formulation are available commercially or may be made by a variety of methods, such as described below or disclosed in Hirao et al., *Polymer* (1986), 27, 309; Nakahama et al., *Macromol. Chem. Macromol Symp.* (1993), 67, 223; Morishima et al., *J. Poly. Sci.: Polymer Chem. Ed.* (1982), 20, 299; and Kamachi et al., *Macromolecules* (1972), 5, 161 all the teachings of which are hereby incorporated by reference.

The term "vinyl N-heterocycle" refers to an ethylene group singly substituted with either a 5-membered aromatic heterocyclic ring containing one to two nitrogens or a 6-membered aromatic heterocyclic ring containing one to three nitrogens. At least one of the nitrogens in the heterocycle must be able to form an addition salt with an organic or inorganic acid. The N-heterocycle may be unsubstituted or substituted with simple alkyl groups. The 5-membered N-heterocycle may be attached by any of its carbon or nitrogen atoms to the vinyl group provided that the nitrogen in the ring retain its acid addition salt forming behavior. The 6-membered N-heterocycle may be attached by any of its carbon atoms to the vinyl group. The 5- or 6-membered heterocyclic groups which may be used include pyridine, pyridazine, pyrimidine, pyrazine, s-triazine, pyrrole, imidazole and pyrazole.

The ratio poly(vinyl N-heterocycle) block size:poly (alkylene oxide) block size may be varied according to the pH dependent properties desired for the final formulation. It should be understood that the present copolymers are diblock copolymers; therefore, they possess a 1:1 incorporation ratio for the respective blocks. When a poly(vinyl N-heterocycle) homopolymer is mixed with the copolymer, the ratio of total poly(vinyl N-heterocycle) to total poly (alkylene oxide) exceed 1:1.

The pH dependent copolymers of formula I may be prepared by a number of means as described in the examples below. Without limitation and by way of example, the general method for preparation of the copolymers follows the scheme below for preparation of a poly(vinyl pyridine)-block-poly(ethylene oxide) copolymer.

It should be understood that the polymerization initiator, which caps one end of the poly(vinyl pyridine) block may be any equivalent compound used for initiating polymerizations. Such equivalent compounds include, for example, s-butyl lithium, n-butyl lithium, cumyl potassium, 1,1-diphenyl-3-methylpentyl lithium, diphenylmethyl lithium, phenyl methide lithium, alkoxides and the like. Alkali based metals such as cesium, sodium, lithium and potassium can be used to generate the initiators. If needed, the named initiators may be mixed with compounds such as 1-aryl-1-phenylethylene, where aryl is naphthyl, phenanthryl, anthracyl, or the like. It should be understood that chelating compounds other than 18-crown-6 may be used. Such other chelating agents are disclosed in Topics in Weber et al., *Current Chemistry* (1981), 98, 1–35 the teachings of which are hereby incorporated by reference.

The pH dependent homopolymers of formula II may be prepared according to the first few steps of the above scheme by quenching the polymerized poly(vinyl N-heterocycle) with a hydrogen source rather than reacting it with an alkylene oxide.

The molecular weight of the poly(vinyl N-heterocycle) is controlled by varying the ratio concentration of monomer::concentration of initiator. Such methods of control are taught in M. Morton, Anionic Polymerizations: Principles and Practice (Academic Press, N.Y., 1983).

Figure 1:
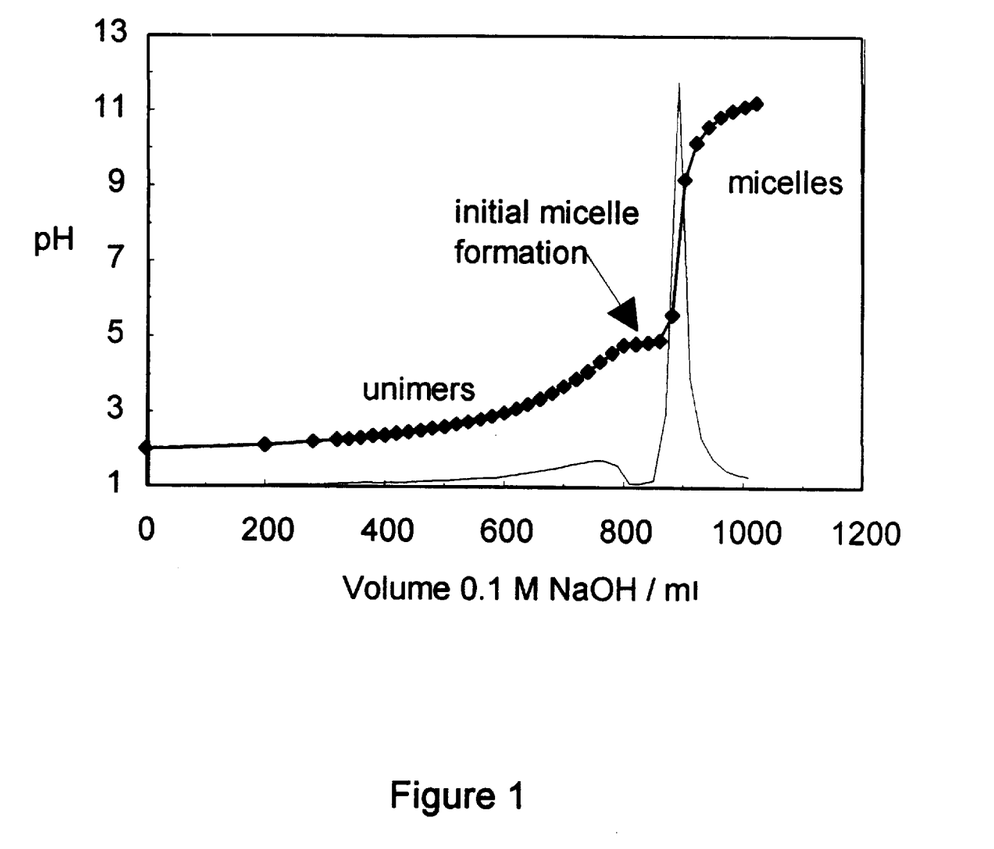
FIG. 1. Acid-base titration curve and first derivative plot of PVP-PEO with 0.1 M NaOH.

An example of the pH dependent micelle formation behavior possessed by the formulation of the invention is shown in FIG. 1 where a poly(vinylpyridine)-block-poly(ethylene oxide) (PVP-PEO) copolymer is titrated with aqueous sodium hydroxide. Titrating an initially acidic solution containing PVP-PEO with base, micelle formation begins at a pH that approximates the pKa of the PVP nitrogens.

It should be understood that the pKa of the nitrogen(s) in the poly(vinyl N-heterocycle) block may be different than that for the respective vinyl N-heterocycle monomer. The pKa of the poly(vinyl N-heterocycle) block should be determined prior to use in a micelle containing formulation. An exemplary method for determining the pKa is detailed below.

The micelles containing a therapeutic compound and a pH dependent poly(vinyl N-heterocycle)-block-poly(alkylene oxide) copolymer of formula I may be prepared by a number of means as described in the examples below. The two general methods are "titration" and "direct dissolution". The N-heterocyclic groups of the micelles need not be completely protonated in order to disrupt the micellular structure.

Figure 2:
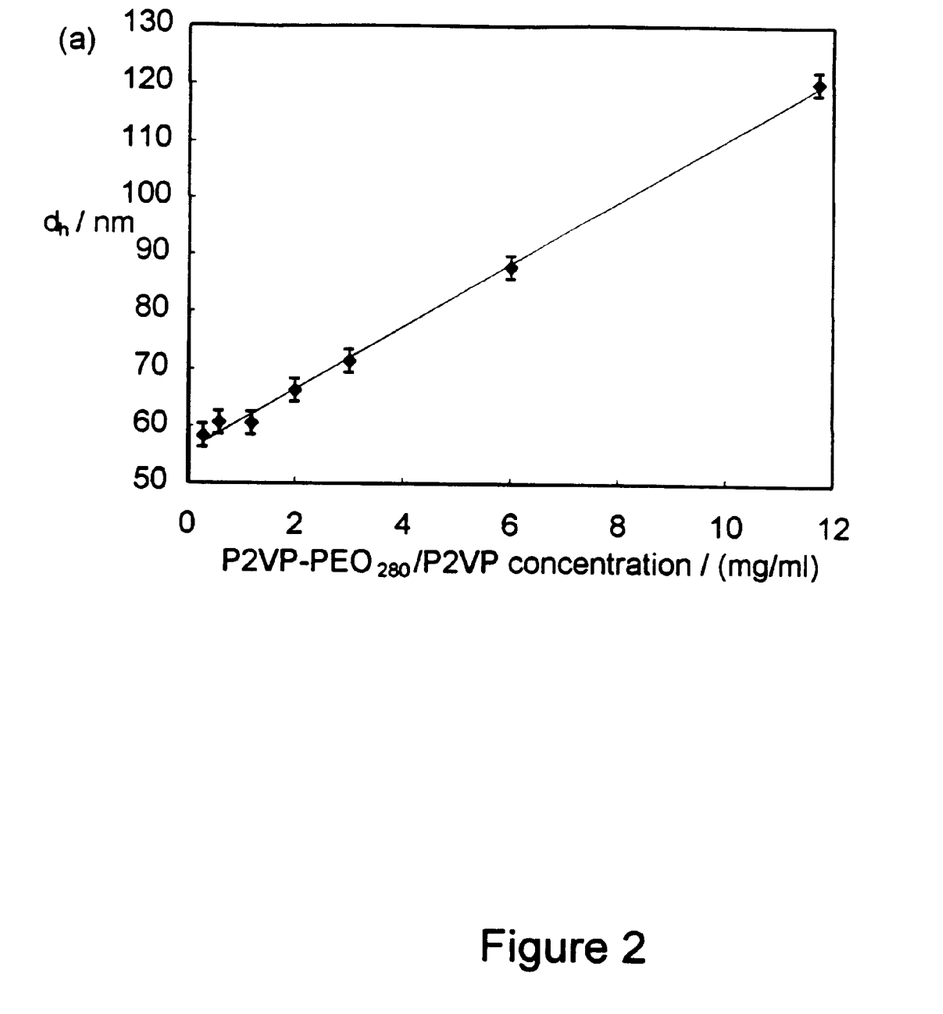
FIG. 2. Plot of micelle hydrodynamic volume vs total initial polymer concentration at elevated pH and constant copolymer:homopolymer ratio of 1:1.
Figure 3:
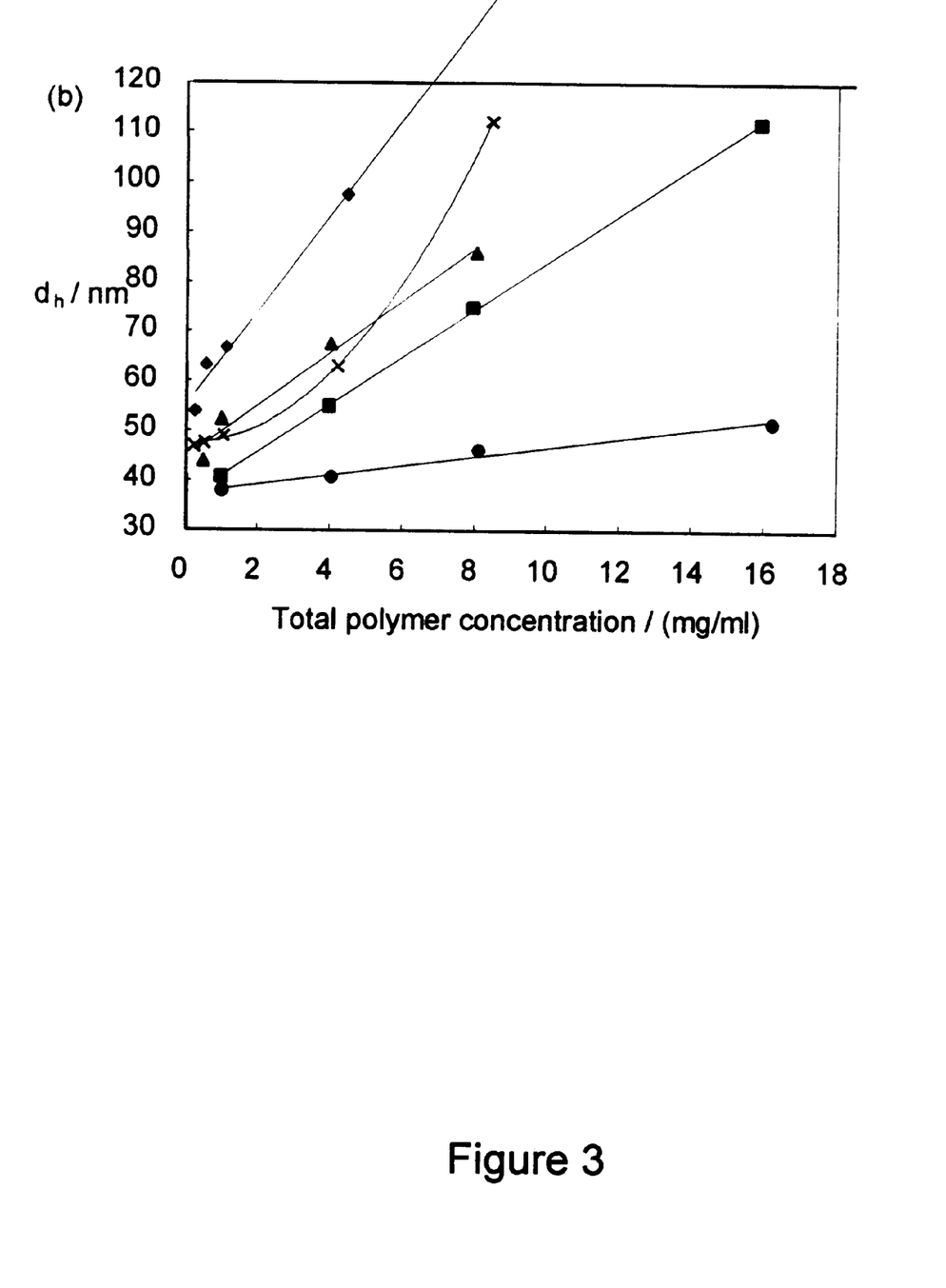
FIG. 3. Plot of micelle hydrodynamic volume vs total polymer concentration using various copolymer:homopolymer ratios as indicated in the inset; where ■ equals 3.96, X equals 1.71, ▲ equals 1.05, ■ equals 0.534 and ● equals 0.0.

When preparing micelles by the titration method below, the final micelle size does not generally vary significantly with the rate of basification. The micelle size may depend upon the amount of poly(vinyl N-heterocycle) homopolymer mixed with the copolymer. FIG. 2 shows the effect initial total polymer concentration has upon the micelle hydrodynamic volume when the P2VP-PEO$_{280}$/P2VP ratio is held constant at 1:1 and a pH of 9 to 11 is used. FIG. 3 shows the combined effect that varying the copolymer:homopolymer ratio and the total polymer concentration has upon the micelle hydrodynamic volume size. Micelle size may also be increased by letting the micelles form at a pH that approximates the pKa of the N-heterocycle nitrogen.

Loading of the micelles with therapeutic compounds may be accomplished following the techniques below for the loading of hydrophobic compounds. Therapeutic compound loading into the micelles may be facilitated by also loading some poly(vinyl N-heterocycle) homopolymer into the micelles. It should be understood that the amount of compound loading into the micelle will vary according to, for example, homopolymer: copolymer ratio therapeutic compound:copolymer ratio in solution used to prepare the micelle, N-heterocycle structure, individual block size of the diblock copolymer and Ltherapeutic compound structure. Although a given loading method may be optimal for a particular hydrophobic compound-copolymer combination, all of the described methods will generally result in compound loading to some degree.

During synthetic manipulation, the vinyl N-heterocycles may possess protecting groups attached to their nitrogens. The various protecting groups contemplated for the synthetic procedures herein are disclosed in "Protective Groups in Organic Synthesis" (T. W. Greene; John Wiley and Sons, New York, N.Y. 1981) and "The Peptides: Analysis, Synthesis, Biology", Vol. 3 (Academic Press, New York, N.Y. 1981) the disclosures of which are hereby incorporated by reference.

The therapeutic compounds loaded into the micelles of the invention may be used for treating indications such as, by way of example and without limitation, inflammation, gout, hypercholesterolemia, microbial infection, AIDS, tuberculosis, fungal infection, cancer, tumor, organ rejection, diabetes, heart failure, arthritis, asthma, urinary tract infections, vaginal infections, seizure related disorders, depression, psychosis, hypertension and birth control.

The hydrophobic therapeutic compounds contemplated within the scope of the invention include, by way of example and without limitation, sulindac, colchicine, clofibrate, probucol, sulfinpyrazone, methicillin, tetracycline, chloramphenicol, rifampin, griseofulvin, etoposide, daunorubicin, doxorubicin, cyclosporin, losoxanthrone, tolbutamide and other structurally related compounds. The hydrophobic compounds may contain aromatic, peptide, hydrocarbon or other such functional groups which generally render compounds hydrophobic. The hydrophobic compounds may possess water solubility to some degree especially when the water is mixed with organic solvents.

Due to the extremely diverse structures found within the broad class of hydrophobic therapeutic compounds, it is likely that particular optimal therapeutic compound/poly(vinyl N-heterocycle)-block-poly(alkylene oxide) combinations will need to be prepared. Such optimal combinations are easily determined and prepared using the methods detailed below.

The following abbreviations may be used herein and are defined as follows:

| | |
|---|---|
| A-PVP | anthracene labelled poly(2-vinlypyridine) homopolymer; |
| DPA | 9,10-diphenylanthracene; |
| EO | ethylene oxide; |
| GPC | gel permeation chromatography; |
| MW | molecular weight; |
| Pd$_{qels}$ | polydispersity as measured by QELS; |
| PVP-PEO | poly(vinylpyridine)-block-poly(ethylene oxide) copolymer; |
| P2VP-PEO | poly(2-vinylpyridine)-block-poly(ethylene oxide) copolymer; |
| QELS | quasi-electric light scattering; and |
| 2VP | 2-vinylpyridine. |

It will be appreciated that certain compounds of the present invention which are used as monomers contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is pyridine, unless specified otherwise, the pyridine group may be bonded to the vinyl group via any carbon atom in such pyridine group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound.

As used herein, "alkyl" is intended to include branched or straight-chain saturated aliphatic hydrocarbon groups having the specified number of carbon atoms. "Halo" or "halogen", as used herein, refers to fluoro, chloro, bromo, and iodo; and "counterion" is used to represent a small, negatively charged species such as chloride, bromide, hydroxide, acetate, sulfate, and the like.

The pharmaceutical formulation of the present invention may be administered by a variety of methods. Such methods include, by way of example and without limitation: intraperitoneal, intra-articular, intra-arterial, intracardiac, intracavity, intracartilaginous, intradermal, intrathecal, intraocular, intraspinal, intrasynovial, intrathoracic, intratracheal, intrauterine, epidural, percutaneous, intravascular, intravenous, intracoronary, intramuscular or subcutaneous injection; inhalation; or oral, nasal, buccal, rectal ophthalmic, otic, urethral, vaginal, or sublingual dosage administration. Such methods of administration and others contemplated within the scope of the present invention are known to the skilled artisan.

In vivo stability of the present formulation may vary according to the physiological environment to which it is exposed and the specific therapeutic, vinyl N-heterocycle and alkylene oxide compounds used. Therefore, the necessity for or frequency of readministration may be different for various formulations.

It is known that cancer, carcinoma and tumor cells have somewhat porous vascularization and are able to incorporate into their cellular endoplasm, by endocytosis, nanometer sized micelles. It is also known, that the hypoxic nature of cancer and tumor cells, generally render the cellular endoplasm more acidic than the surrounding physiological environment. For these reasons, it is anticipated, the present formulation will be particularly well suited for selected delivery of drugs to cancer, tumor or carcinoma containing tissues.

The micelles used in the present invention may be formulated in a variety of ways. Any ingredients used in the present formulation should not disrupt micellular structure to any great extent, so that at least a significant portion of the micelles will be mintact prior to administration. For injection, the micelles may be formulated, for reconstitution with an appropriate solution, as, for example and without limitation: freeze dried, rotary dried or spray dried powders; amorphous powders; or granules, precipitates or particulates. For injection, the micelles may also be formulated as suspensions or liquids in the appropriate solutions, such as, by way of example and without limitation, water, aqueous solvents, nonprotic solvents, protic solvents, hydrophilic solvents, hydrophobic solvents, polar solvents, nonpolar solvent and/or combinations thereof, optionally containing stabilizers, pH modifiers, surfactants, bioavailability modifiers and/or combinations thereof. The only requirements are that the pH dependent nature of the micelle not be lost and that the micelles retain their integrity prior to administration. The micelles can be administered in the form of a depot injection or implant preparation which may be formulated in such a manner as to permit a sustained release of the active ingredient. The formulation can be compressed into pellets or small cylinders and implanted subcutaneously or intramuscularly as depot injections or implants. Implants may employ inert materials such as biodegradable polymers or synthetic silicones, for examples, Silastic, silicone rubber-manufactured by the Dow-Corning Corporation.

For inhalation either nasally or orally, the micelles of the invention may be formulated as sprays or aerosols containing the appropriate solvents (such as water, aqueous, nonaqueous, polar, nonpolar, hydropic, hydrophilic and/or combinations thereof) and optionally other compounds (stabilizers, perfumes, antimicrobial agents, antioxdants, pH modifiers, surfactants and/or bioavailability modifiers). A propellant such as compressed air, nitrogen, carbon dioxide or hydrocarbon based low boiling solvents (such as butane, propane or others) would be used in an aerosol formulation.

For nasal administration, the same type of formulations used for the inhalation administration may be used. In addition, pastes, ointments or creams containing the micelles of the invention may also be used. It is contemplated that bioavailability enhancers such as alcohols or other compounds that enhance the penetration of the micelles into the nasal mucosa may be needed to prepare suitable formulations for nasal administration.

For oral, buccal, and sublingual administration, the micelles of the invention may be administered as either solutions or suspensions in the form of gelcaps, caplets, tablets, capsules or powders. For rectal administration, the compounds of the invention may be administered in the form of suppositories, ointments, enemas, tablets and creams for release of compound in the intestines, sigmoid flexure and/or rectum. It is contemplated that the micelles may be formulated as for example and without limitation: freeze dried, rotary dried or spray dried powders; amorphous or crystalline powders; or granules, precipitates or particulates. The solids used may be either free-flowing or compressed. The compounds may also be formulated as ointments, creams, gels, slurries, suspensions or liquids in solutions, such as, by way of example and without limitation, water, aqueous solvents, nonprotic solvents, protic solvents, hydrophilic solvents, hydrophobic solvents, polar solvents, nonpolar solvent, emollients and/or combinations thereof, optionally containing stabilizers, pH modifiers, surfactants, perfumes, astringents, cosmetic foundations, pigments, dyes, bioavailability modifiers and/or combinations thereof.

In solid unit dosage forms the compounds can be combined with conventional carriers, for example, binders, such as acacia, corn starch or gelatin; disintegrating agents, such as, corn starch, guar gum, potato starch or alginic acid; lubricants, such as, stearic acid or magnesium stearate; and inert fillers, such as lactose, sucrose or corn starch. These carriers should not disrupt a significant portion of the micelles.

The term "unit dosage form" is used herein to mean a single or multiple dose form containing a quantity of the micelle containing formulation, said quantity being such that one or more predetermined units are normally required for a single therapeutic administration. In the case of multiple dose forms, such as liquids or scored tablets, said predetermined unit will be one fraction such as 5 ml (teaspoon) quantity of a liquid or a half or quarter of a scored tablet, of the multiple dose form.

The compounds of general Formula I may also be administered as liquid suspensions or solutions using a sterile liquid, such as an oil, water, an alcohol, or mixtures thereof, with or without the addition of a pharmaceutically suitable surfactants, suspending agent, or emulsifying agent for oral or parenteral administration.

For liquid preparations, the compounds of Formula I can be formulated suitably with oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides; with alcohols, such as ethanol, isopropanol, hexadecyl alcohol, glycerol and propylene glycol; with glycerol ketals, such as 2,2-dimethyl-1,3-dioxolane-4-methanol; with ethers, such as poly (ethyleneglycol) 450, with petroleum hydrocarbons, such as mineral oil and petrolatum; with water, or with mixtures thereof; with or without the addition of a pharmaceutically suitable surfactant, suspending agent or emulsifying agent. The only requirements are that the pH dependent behavior of the micelles not be lost and that a significant portion of the micelles remain present prior to administration.

Oils can also be employed in the preparation of formulations of the soft gelatin type and suppositories. Water, saline, aqueous dextrose and related sugar solutions, and glycerols, such as polyehtyleneglycol, may be employed in the preparation of liquid formulations which may suitably contain suspending agents, such as pectin, carbomers, methyl cellulose, hydroxypropyl cellulose or carboxymethyl cellulose, as well as buffers and preservatives. Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; non-ionic detergents, for example, fatty amine oxides, fatty acid alkanolamides, and polyoxyethylenepolyoxypropylene copolymers; and amphoteric detergents, for example, alkyl β-aminopropionates and 2-alkylimidazoline quaternary ammonium salts; and mixtures thereof. The only requirements are that the pH dependent behavior of the micelles not be lost and that a significant portion of the micelles remain present prior to administration.

It is contemplated that either one or a combination of short-acting, long-acting, sustained release, controlled release, pulsated release or slow release dosage forms may be used in the present invention. The course and duration of administration of and the dosage requirements for the micelles of the present invention will vary according to the subject being treated, the compound being administered, the formulation used, the method of administration used, the severity and type of indication being treated, the coadministration of other drags and other factors.

The therapeutic compounds contained within the micelles may be formulated as their pharmaceutically acceptable salts. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a predetermined amount of the appropriate base or acid in water or in an organic solvent, or in a mixture of the two. Generally, nonaqueous media are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In some embodiments, the invention comprises a micelle containing pharmaceutical formulation that includes a therapeutic compound and a poly(vinyl N-heterocycle)-block-poly(alkylene oxide) copolymer, where the copolymer is selected from a compound of the formula I $$R_1-[CH_2CH(R_2)]_m-[CH_2CH(R_3)O]_n-H \qquad \text{Formula I}$$

and all its isomeric, chiral, pharmaceutically acceptable salt, oligomeric, polymeric, diastereomeric and/or racemic forms wherein:

$R_1$ is H or a polymerization initiator selected from the group consisting of:
cumyl, s-butyl, n-butyl, 1,1-diphenylethyl, 1-phenyl-1-naphthylethyl, 1-phenyl-1-phen-phenanthrylethyl, 1-anthracyl-phenylethyl, 2-phenylpropyl or diphenylmethyl;

$R_2$ is selected from the group consisting of:

$R_3$ is H or C1–C5 alkyl;

$R_5$ is H or C1–C5 alkyl attached to any carbon or $R_2$;

m is independently selected at each occurrence from 50 to 400; and n is independently selected at each occurrence from 50 to 400;

provided the ability of the copolymer to form micelles is pH dependent and the resulting compound is stable.

In other embodiments, the invention comprises a micelle containing pharmaceutical formulation that includes a therapeutic compound, a poly(vinyl N-heterocycle) homopolymer and a poly(vinyl N-heterocycle)-block-poly(alkylene oxide) copolymer, where the copolymer is selected from a compound of the formula I wherein:

$R_2$ is selected from the group consisting of:

$R_3$ is H or C1–C5 alkyl;

$R_5$ is H;

m is independently selected at each occurrence from 50 to 300; and n is independently selected at each occurrence from 50 to 300; and where the homopolymer is selected from a compound of the formula II and all its isomeric, chiral, pharmaceutically acceptable salt, oligomeric, polymeric, diastereomeric and/or racemic forms wherein:

$R_1$ is H or a polymerization initiator selected from:
cumyl, s-butyl, n-butyl, 1,1-diphenylethyl, 1-phenyl-1-naphthylethyl, 1-phenyl-1-phenanthrylethyl, 1-anthracyl-phenylethyl or diphenylmethyl;

$R_2$ is selected from the group consisting of:

$R_3$ is H or C1–C5 alkyl;

$R_5$ is H or C1–C5 alkyl attached to any carbon on $R_2$; and m is independently selected at each occurrence from 50 to 300.

In yet other embodiments, the micelle containing pharmaceutical formulation comprises a therapeutic compound and a poly(vinyl N-heterocycle)-block-poly(alkylene oxide) copolymer, where the copolymer is selected from a compound of the formula I wherein:

$R_2$ is selected from the group consisting of:

$R_3$ is H or C1–C5 alkyl.

The micelle containing pharmaceutical formulation may also comprise a therapeutic compound and a poly(vinyl N-heterocycle)-block-poly(ethylene oxide) copolymer, where the copolymer is selected from a compound of the formula I wherein:

$R_2$ is pyridine; and $R_3$ is H.

Unless otherwise indicated, all chemicals were purchased from Aldrich Chemicals (Milwaukee, Wis.).

EXAMPLE 1

Analytical Methods used to Characterize the Polymers and Copolymers

The gel permeation chromatography (GPC) system consisted of a Waters pump (Model 510) and four Waters Millipore μStyragel columns ($10^5$, $10^4$, $10^3$, 500 Å, in order of flow) using UV-Vis absorption, fluorescence and refractive index detectors, sequentially. A Hewlett Packard Vectra 486DX4-100 computer supplied with the HP 1050 Diode Array Detector was equipped with an A/D board used to simultaneously record the analog output from the Waters Differential Refractometer R401 and the Perkin-Elmer LS-1 Fluorescence Detector. THF was used for the mobile phase at a flow rate of 1.5 ml/min. Polystyrene standards (Scientific Polymer Products) were used for calibration. For most detectors used in GPC systems, the detector response is proportional to the weight of the polymer sample (differential refractive index; light scattering; absorbance or fluorescence of chromophores that vary proportionally with the degree of polymerization). The average molecular weight moments were calculated with this assumption of detector response.

All NMR measurements were performed on a Bruker AC-250 Spectrometer (250 MHz). The spectra were referenced to residual solvent protons. A ratio of the area under the aromatic region and the t-butyl peak for the unhydrolyzed polymer samples was compared to the ratio derived from the GPC data. This comparison was used to verify values obtained for mole and weight fractions of the individual copolymer blocks.

EXAMPLE 2

Preparation of Initiators used to Prepare

Poly(2-vinylpyridine)-block-poly(ethylene oxide) 1-(1-Hydroxy-1-methylethyl)naphthalene. A 10 ml (65.8 mmole) quantity of 1-acetonaphthone was dissolved in 150 ml of diethyl ether in a 500 ml, two neck, round bottom flask equipped with a pressure equalizing dropping finnel and fitted with a rubber septum and a protected reflux condenser. A 138 ml (98 mmole) quantity of 1.4 M methyllithium in ether (Aldrich) was transferred to the fiumel by use of a cannula and nitrogen pressure. This was slowly added to the stirred ketone over a 20 minute period. A light green color indicated an excess of methyllithium. This was refluxed for an additional hour and the reaction was carefully quenched with water. The ether layer was made acidic using HCl, neutralized with $NaHCO_3$, dried using $MgSO_4$, and filtered. After the solvent was removed, the crude product was recrystallized from benzene, filtered and washed with cold pentane to yield white, fibrous crystals (>98%), m.p. 81–86° C. 1H NMR (acetone-d6): (=9.01 (m, 1 H, aromatic), 7.95 (m, 1 H, aromatic), 7.82 (d, J=10.6, 1 H, aromatic), 7.68 (d, J=10.3, 1 H, aromatic), 7.50 (m, 3 H, aromatic), 4.30 (s, 1 H, —OH), 1.84 (s, 6 H, —CH3).

1-(1-Methoxy-1-methylethyl)naphthalene. A 12 g (64.4 mmole) quantity of the compound made above was dissolved in 300 ml of THF employing the above setup without the funnel. About 2 g of NaH was slowly added to the stirred solution. An excess was added once the $H_2$ evolution ceased such that solid NaH settled on the bottom of the flask. A 8.1 ml (130 mmole) quantity of methyliodide was added at once, and the mixture was stirred at room temperature overnight. (Methyl tosylate works in place of $CH_3I$, but the excess is difficult to remove.) This mixture was then acidified, neutralized, and isolated as described above. The crude, oily product was put through an $Al_2O_3$ column, eluted with hexane to remove the starting material (>90% yield). $^1$HNMR (acetone-d6): (=8.95 (m, 1 H, aromatic), 7.84 (m, 2 H, aromatic), 7.44 (m, 4 H, aromatic), 2.95 (s, 3 H, —OCH3), 1.73 (s, 6 H, —CH3). MS (CI+): m/z=200 (M+), 185 (M+ —CH3), 169 (M+ —OCH3).

Naphthylisopropyl potassium. The just prepared ether was reacted just as its cumyl analog to form the initiator. Potassium was cut under mineral oil and washed with hexane. It was placed in the reaction vessel and sublimed under dynamic vacuum to form a mirror. The was distilled in and 2 was added. A deep red-orange color appeared immediately. The solution was stirred overnight at room temperature and filtered to remove the precipitated MeOK. It was transferred to a pressure equalizing dropping funnel and protected from light. A fraction of this was titrated with acetanilide to calculate the molarity. Another portion was terminated with degassed methanol for structural analysis. 1H NMR (acetone-d6): (=8.18 (m, 1 H, aromatic), 7.90 (m, 1 H, aromatic), 7.74 (m, 1 H, aromatic), 7.50 (m, 4 H, aromatic), 3.78 (m, 1 H, —CH), 1.38 (d, 6 H, CH3). MS (CI+): m/z=170 (M+), 155 (M+ —CH3), 140, 129 (M+ —CH (CH3)2).

1,1-Diphenyl-3-methylpentollithium. 1,1-Diphenylethylene (DPE) (Aldrich) was purified by vacuum distillation from s-butyl lithium (b.p. 75° C. at 1×10-3 torr). When s-butyl lithium was added to impure DPE, a green color appears first which turns to red/orange upon further addition. The green color is due to the benzophenone impurity. The DPE distillate was stored at 5° C. under N2 away from light. The molarity of s-butyl lithium (ca. 1.3 M in cyclohexane) was determined by titration with 0.1 ml of 2,5-dimethoxybenzyl alcohol to a red end-point indicating the dianion of the alcohol. 1.0 mmoles of s-butyl lithium of known concentration was added to a flame-treated ampule containing 25.0 ml THF and 0.35 ml (2.0 mmole) purified DPE. It is often convenient to dilute s-butyl lithium as received by 10 or 20 fold with cyclohexane so that larger, more accurate volumes could be measured. Alternatively, exact amounts of DPE dissolved in THF and s-butyl lithium needed for the polymerization could be added directly to the polymerization reactor after the solvent has been distilled in. Due to the reactivity of s-butyl lithium, it should not be added to THF without DPE present.

EXAMPLE 3

Preparation of Poly(2-vinylpyridine)-block-poly (ethylene oxide): P2VP-PEO

A 10:1 molar ratio of 18-crown-6 ether to cumyl potassium was added to the reactor in order to activate the propagating species. 18-crown-6 was added to the flame treated reactor and a dynamic vacuum was applied to degas and dry the ether. THF was distilled in and titrated. A larger than usual amount of the initiator was needed to titrate the reaction solvent due to the remaining impurities in the 18-crown-6.2VP was added dropwise to a solution of the activated initiator and allowed to react 30 minutes. An aliquot was withdrawn at this point and terminated with MeOH. After the addition of ethylene oxide, the reaction was allowed to proceed 40 to 48 hours. The P2VP anion color faded over a period of one half hour. The dry ice/isopropyl alcohol bath remained in place but no additional dry ice was added over this period of time. This allowed the polymerization solution to slowly rise to room temperature. This elevated temperature was necessary for EO to polymerize to high molecular weights. The polymerization reactor was under pressure at 25° C. due to the increased vapor pressure of both the THF and EO (b.p.=10° C. at 1 atm.). However, some fraction of EO was constantly present in solution (Henry's Law) and able to be polymerized. The anion was terminated with 0.5 ml MeOH. The copolymer was recovered by precipitation in hexane and the aliquot was precipitated in H2O.

The P2VP-PEO sample contained a significant amount of P2VP homopolymer. The homopolymer was removed by fractional precipitation. A 0.61 g quantity of P2VP-PEO$_{280}$ containing approximately 1:1 mole ratio of homopolymer to copolymer was dissolved in 13.0 ml of benzene at room temperature. A 3.3 ml quantity of isooctane was added dropwise. The precipitate (mostly homopolymer) was allowed to settle 24–48 hours. The supernatant was carefully decanted and freeze-dried. There was evidence by GPC that a low molecular weight peak at about 5,000 g/mole appears if the solution was not allowed to settle or was not centrifuged adequately. This was due to lower molecular weight P2VP remaining suspended. This process of dissolving in benzene and precipitation was repeated until the GPC chromatogram for the copolymer was monomodal or unchanged.

TABLE 1

GPC Results for Diblock Copolymer Synthesis

| Polymer | RI[a] $<MW>_n$[c] | PD | Fluor.[b] $<MW>_n$ | PD | OD[f] $<MW>_n$ | PD | Targ. MW |
|---|---|---|---|---|---|---|---|
| PVP | 14,000 | 1.1 | — | — | 14,000 | 1.1 | 25K |
| PVP-PEO[e] | 16,500 | 1.2 | — | — | 17,000 | 1.2 | 50K |
| PVP | 25,000 | 1.0 | — | — | 25,000 | 1.0 | 30K |
| A-PVP | 55,000 | 1.1 | 52,000 | 1.37[d] | 53,000 | 1.1 | 35K |

[a]Differential refractive index detection.
[b]Number average molecular weight (g/mole) and polydispersity, PD = $<M>_w$/$<M>_n$
[c]Number average molecular weight (g/mole) and polydispersity, PD = $<M>_w$/$<M>_n$ computed from a PS calibration curve and taking the RI signal to be properitoneal to the polymer weight, as is stand procedure
[d]Signifies an excess of fluorescent monomer which causes "tailing" in chromatogram.
[e]Values include shoulder, maximum value = 28,000 g/mole.
[f]Optical density at 260 nm.

TABLE 2

Physical Data for PVP Containing Copolymers

| Polymer | For PVP block | | | 2VP/EO[c] |
|---|---|---|---|---|
| | <MW>$_n$[b] | PD | x[d] | |
| PVP-PEO$_{280}$[a] | 14,000 | 1.18 | 0.53 | 0.48 |
| PP-PEO$_{350}$[a] | 14,000 | 1.07 | 0.47 | 0.38 |

[a]Since the PVP blocks have similar molecular weights (DP$_{>n}$ = 133 for both), each PVP-PEO copolymer is distinguished by the DP of the PEO block.
[b]Number average molecular weight for the PVP block by GPC.
[c]Monomer ratio in the copolymer (purified when necessary) by NMR.
[d]Weight fraction of PVP in copolymer.

TABLE 3

Data for Comparison of Micelle Preparation Methods

| Method | [PVP-PEO][a] | d$_h$[e] | I$_{QELS}$[f] | OD(325)[b] | pyrene[d] (%) | I$_1$/I$_3$[c] |
|---|---|---|---|---|---|---|
| Direct | 0.44 | 72.2 | | | | |
| | 0.96 | | | | | |
| | 1.98 | | | | | |
| | 4.12 | | | | | |
| Titration | 0.46 | 51.7 | 28 | 0.0319 | 1.01 (0.27) | 1.5 |
| | 1.00 | 48.9 | 62 | 0.116 | 3.66 (0.96) | 1.4 |
| | 2.06 | 53.8 | 156 | 0.383 | 12.1 (3.2) | 1.4 |
| | 3.90 | 49.8 | 244 | 0.941 | 29.7 (7.8) | 1.4 |

[a]PVP-PEO$_{350}$ concentration in mg/ml.
[b]Corrected optical density at 325 mm for pyrene-loaded PVP-PEO micelles. Note that the intrinsic solubility of pyrene yields an OD of ca. 0.02, so that a factor of ca. 50 solubilization improvement is obtained. This improvement should scale with the total micelle concentration.
[c]I$_1$/I$_3$ ratio for pyrene. No excimer emission is observed.
[d]Mass of pyrene in micrograms in 5.00 ml of the micelle solution. The values in parenthesis are the percent of the total available pyrene found in the micelle.
[e]Hydrodynamic diameter of micelle by QELS in nm.
[f]Scattering intensity of micelles by QELS in Kcounts/sec.

EXAMPLE 4

Preparation of Micelles by Titration

In general, the desired amount of P2VP-PEO (usually 5.0 mg) was dissolved in 5.0 ml 0.1 M HCl (resulting pH is ~1). Next, 0.1 M NaOH was added dropwise to a vigorously stirred solution as the pH is monitored. If a titration curve was to be generated, the base was added in 20 µl increments and the pH was recorded on the HP computer. As the titration approached the point at which micelles form (pH ~4.0–4.9) for the more concentrated solutions, blue swirls were observed in the solution due to scattering by micelles. This scattering was allowed to dissipate as the solution homogenized before the next quantity of base was added. The titration was stopped at the desired pH (ca. 7, 9 or 11).

EXAMPLE 5

Preparation and Loading of Micelles by Direct Dissolution

The P2VP-PEO$_{350}$ copolymer was soluble directly in deionized water, regardless of its morphological state. Micelles formed spontaneously. A 5.0 mg quantity of P2VP-PEO$_{350}$ was simply added to 5.0 ml of deionized water and agitated until dissolved. When a hydrophobic substance (DPA, pyrene, etc.) was to be loaded into the micelle core, it was dissolved in benzene along with the desired ratio of polymer. The solution was freeze-dried and the resulting solid was redispersed in deionized water with a significant retention of the hydrophobic species.

EXAMPLE 6

Preparation of P2VP-PEO HCl Salt

The HCl polymer salt i.e., P(2VP.HCl)-PEO, was produced by dissolving the neutral polymer in 1,4-dioxane and adding concentrated HCl (38%). The P(2VP.HCl)-PEO precipitated from dioxane into the water layer which was separated and freeze-dried. A 20 mg quantity of P2VP-PEO was precipitated from 15 ml 1,4-dioxane. The freeze-dried sample dissolved molecularly (unimerically) in 16 ml of water with a resulting pH of 2.5. No scattering was observed in this solution. This was basified as above to produce micelles.

EXAMPLE 7

Loading of Hydrophobic Compound into Micelles: Simple Mixing

A micelle containing solution (at a pH above the pKa for the N-heterocycle nitrogen, about a pH of 5) is stirred in an aqueous solution in the presence of the hydrophobic compound. After equilibration, the micelles are separated from undissolved hydrophobic compound by conventional microfiltration (0.45 µm pore size). This method generally works for hydrophobic compounds exhibiting some degree of water solubility.

EXAMPLE 8

Loading of Hydrophobic Compound into Micelles: Biphasic System

The hydrophobic compound is dissolved in high concentrations in a water immiscible organic solvent. An aqueous solution containing PVP-PEO micelles contained in a dialysis tube is place in contact with the organic solvent. After equilibration, the dialysis tubing containing micelles is removed.

EXAMPLE 9

Loading of Hydrophobic Compound into Micelles: Cotitration

An initially acidic aqueous solution containing PVP-PEO is mixed with a hydrophobic compound. The solution pH is raised by the addition of a base to at least about a pH of 5. Upon micelle formation, the hydrophobic compound is incorporated into the micelles which are separated from the solution using conventional methods.

EXAMPLE 10

Loading of 9,10-Diphenylantracene (DPA) into Micelles: Direct Dissolution of Freeze Dried Solid A known quantity of DPA is dissolved in a known quantity of benzene. PVP-PEO$_{350}$, at a loading of 5 mg/mL of solution, is added to the benzene and the mixture stirred. Following equilibration, the solution is freeze dried. The solid is then suspended in water, to a concentration of 1 mg solids/mL of solution, and filtered. Analysis reveals approximately 24% of the DPA was loaded into the micelles. The micelles are stable with respect to aggregation and DPA loading.

EXAMPLE 11

Loading of Pyrene into Micelles:

Direct Dissolution of Freeze Dried Solid

The above procedure for DPA is followed for loading pyrene into the micelles. Analysis reveals approximately 39% of the pyrene was loaded into the micelles. Emission spectroscopy of the micelles shows a sharp increase in eximer fluorescence of pyrene.

EXAMPLE 12

Methods for the Isolation of Micelles

Freeze drying. A solution containing micelles loaded with hydrophobic compound may be freeze dried. An aqueous suspension of PVP-PEO micelles in a flask is placed in a sub-zero degree Celsius bath until the solution solidifies. The solid is then subjected to high vacuum to remove all solvents leaving the micelles in the flask. As prepared, the micelles are very stable.

Filtration. An aqueous suspension of 9,10-diphenylanthracene (DPA) containing P2VP-PEO micelles is passed through an 0.45 μm filter which retains the DPA crystals and allows passage of the micelles.

EXAMPLE 13

General Method for the Preparation of Therapeutic Compound/Poly(vinyl N-heterocycle) Homopolymer/Poly(vinyl N-heterocycle) block-poly(alkylene oxide) Combinations Selection of a particular poly(vinyl N-heterocycle)-block-poly(alkylene oxide)/therapeutic compound combination is done by determining the relative solubility of the therapeutic compound in the respective poly(vinly N-heterocycle) homopolymer. Thus, a thin film of the poly(vinyl N-heterocycle) is cast and placed in contact with a solution containing the therapeutic compound. After equilibration, the film and solution are separated, and the film is dissolved in a solvent which will also dissolve the therapeutic compound. The solvent is then analyzed by GPC, and the relative mole fraction of therapeutic compound with respect to homopolymer is determined. A suitable copolymer/therapeutic compound combination will yield the desired mole fraction of therapeutic compound.

EXAMPLE 14

General Method for the Determination of Therapeutic Compound Release Rate

Use of this method allows one to determine the relative stability of a particular therapeutic compound/poly(vinyl N-heterocycle)-block-poly (alkylene oxide) copolymer combination. A known amount of micelle containing powder is placed in dialysis tubing containing a first portion of an aqueous solution. The tubing is then sealed and placed in a second portion of the solvent. The amount of compound released into the second portion is then monitored to develop a time course which reflects the release rate of compound from the micelle.

EXAMPLE 15

Preparation of A Therapeutic Compound/Poly(vinvlpyridine)-block-poly(ethylene oxide)/Poly(vinylpyridine) Homopolymer Formulation A mildly acidic buffered solution containing a known amount of therapeutic compound is premixed with a known amount of poly(vinlypyridine) homopolymer while stirring. A known amount of PVP-PEO copolymer is added until the desired ratios of homopolymer:copolymer and therapeutic compound:copolymer are achieved. The pH of the solution is then raised with base until micelle formation is complete. After equilibration, the micelles are separated from the solution by microfiltration and freeze dried.

EXAMPLE 16

Preparation of A Therapeutic Compound/Poly(vinylplridine)-block-poly(ethylene oxide)/Poly(vinylpyridine) Homopolymer Formulation for Injection A buffered solution (pH <4) containing a known amount of losoxanthrone is mixed with a known amount of PVP homopolymer. A known amount of PVP-PEO copolymer is added until the weight ratio of homopolymer:copolymer is 0.5:1 to 5:1 and the weight ratio of therapeutic compound:total polymer is 1:100 to 50:100. The pH is raised with dilute sodium hydroxide until micelle formation is complete. After equilibration, the micelles and supernatant are separated by filtration and the micelles freeze dried. The micelle containing powder is placed in a vial containing $Na_2HPO_4$ buffer and NaCl. The powder is then reconstituted with saline or other suitable liquid prior to injection.

EXAMPLE 17

Preparation of A Therapeutic Compound/Poly(vinylpyridine)-block-poly(ethylene oxide)/Poly(vinylpyridine) Homopolyrner Formulation for Tablet Sulindac containing freeze dried micellular powder (50–700 mg) is mixed with starch (10–200 mg) and lactose (10–200 mg). After granulation, magnesium stearate (1–20 mg) is added and the powders mixed and screened. The mixture is then compressed into tablets weighing 75–1000 mg each. The tablets are then coated with an enteric coating to minimize gastric dissolution and promote intestinal dissolution.

EXAMPLE 18

Preparation of a Formulation for Hard Gelatin Capsules

A daunorubicin containing freeze dried micellular powder (50–500 mg) is mixed with talc (1–100 mg) and lactose (1–200 mg). The powders are mixed and passed through a fine mesh screen. The powder is then filled into enteric coated hard gelatin capsules at a net fill of 60–800 mg per capsule.

The above is a detailed description of particular embodiments of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. A micelle-containing formulation comprising:
   a pharmacologically active agent; and
   a poly (vinyl N-heterocycle)-block-poly (alkylene oxide) copolymer, wherein said vinyl N-heterocycle) is a 5 or 6 member ring and wherein said copolymer is capable of forming micelles containing the pharmacologically active agent in an environment having a relatively higher pH than the copolymer.

2. A formulation comprising pH-dependent block copolymer micelles.

3. The formulation of claim 2 wherein the block copolymer is a poly (vinyl N-heterocycle)-block-poly (alkylene oxide) copolymer and when said Vinyl N-heterocycle is a 5 or 6 member ring.

4. The formulation of claim 2 wherein the pH-dependent block copolymer micelles further comprise a pharmacologically active agent.

5. The formulation of claim 1 wherein the micelles are further defined as releasing the pharmacologically active agent in an aqueous environment having a relatively lower pH than the copolymer.

6. The formulation of claim 5 wherein the relatively lower pH of the aqueous environment is further defined as a pH of between about 2 to a pH of about 6.

7. A micelle containing pharmaceutical formulation comprising copolymers of formula I below:

Formula I and isomeric, chiral, pharmaceutically acceptable salt, oligomeric, polymeric, diastereomeric or racemic forms thereof, wherein:

$R_1$ is H or a polymerization initiator selected from the group consisting of:
cumyl, s-butyl, n-butyl, 1,1-diphenylethyl, 1-phenyl-1-naphthylethyl, 1-phenyl-1-phenanthrylethyl, 1-anthracyl-phenylethyl, 2-phenylpropyl and diphenylmethyl;

$R_2$ is selected from the group consisting of:

where, for the structures containing an $R_4$ substituted nitrogen, $R_4$ may be absent from the nitrogen and $R_2$ may attach to the structure backbone by way of the nitrogen;

$R_3$ is H or C1–C5 alkyl;

$R_4$ is C1–C5 alkyl when $R_2$ is attached to the copolymer backbone by an atom other than the nitrogen to which $R_4$ is attached;

$R_5$ is H or C1–C5 alkyl attached to any carbon on $R_2$;

m is independently selected at each occurrence from 50 to 500; and n is independently selected at each occurrence from 50 to 500.

8. A micelle containing pharmaceutical formulation comprising homopolymers that include copolymers of the formula II.

Formula II and isomeric, chiral, pharmaceutically acceptable salt, oligomeric, polymeric, diastereomeric or racemic forms thereof, wherein:

$R_1$ is H or a polymerization initiator selected from the group consisting of:
cumyl, s-butyl, n-butyl, 1,1-diphenylethyl, 1-phenyl-1-naphthylethyl, 1-phenyl-1-phenanthrylethyl, 1-anthracyl-1-phenylethyl and diphenylmethyl;

$R_2$ is selected from the group consisting of:

where, for the structures containing an $R_4$ substituted nitrogen, $R_4$ may be absent from the nitrogen and $R_2$ may attach to the structure backbone by way of the nitrogen;

$R_4$ is C1–C5 alkyl when $R_2$ is attached to the copolymer backbone by an atom other than the nitrogen to which $R_4$ is attached;

$R_5$ is H or C1–C5 alkyl attached to any carbon on $R_2$; and m is independently selected at each occurrence from 50 to 500;

to provide a chemically stable compound.

9. A micelle containing pharmaceutical drug delivery formulation comprising a pharmacologically active agent and micelles comprising the copolymers of claim 7, copolymers of claim 8, or a combination thereof, wherein the pharmacologically active agent is released from the micelles in the presence of a decrease in pH.

10. The micelle containing pharmaceutical drug delivery formulation of claim 1, wherein the pharmacologically active agent is an anti-cancer therapeutic agent.

* * * * *